United States Patent [19]
Yan

[11] Patent Number: 5,453,163
[45] Date of Patent: Sep. 26, 1995

[54] ELECTROKINETIC PACKING OF CAPILLARY COLUMNS

[76] Inventor: Chao Yan, 1200 N. Queen St., #108, Arlington, Va. 22209

[21] Appl. No.: 142,917

[22] Filed: Oct. 29, 1993

[51] Int. Cl.$^6$ ........................ B01D 57/00
[52] U.S. Cl. .................. 204/180.1; 204/182.8; 204/299 R; 210/656; 53/473
[58] Field of Search .......... 204/180.1, 182.8, 204/299 R; 210/748, 656; 53/473

[56] References Cited

U.S. PATENT DOCUMENTS

| | | | |
|---|---|---|---|
| 4,483,773 | 11/1984 | Yang | 210/656 |
| 5,080,771 | 1/1992 | Novotny et al. | 204/182.8 |
| 5,135,627 | 8/1992 | Soane | 204/182.8 |

Primary Examiner—John Niebling
Assistant Examiner—C. Delacroix-Muirheid
Attorney, Agent, or Firm—Jacobson, Price, Holman & Stern

[57] ABSTRACT

Capillary columns are packed using electroosmotic flow (EOF) induced by an electrical double layer on the internal wall of a fused silica capillary and the electrophoretic mobility of positively-charged or negatively-charged particles of packing material. Electrokinetic packing is also applicable to uncharged packing particles. With this electrokinetic method several capillaries can be packed simultaneously. Electrokinetically packed capillary columns are useful for the separation of test mixtures and of pharmaceuticals in both electrochromatography and micro-HPLC.

12 Claims, 4 Drawing Sheets

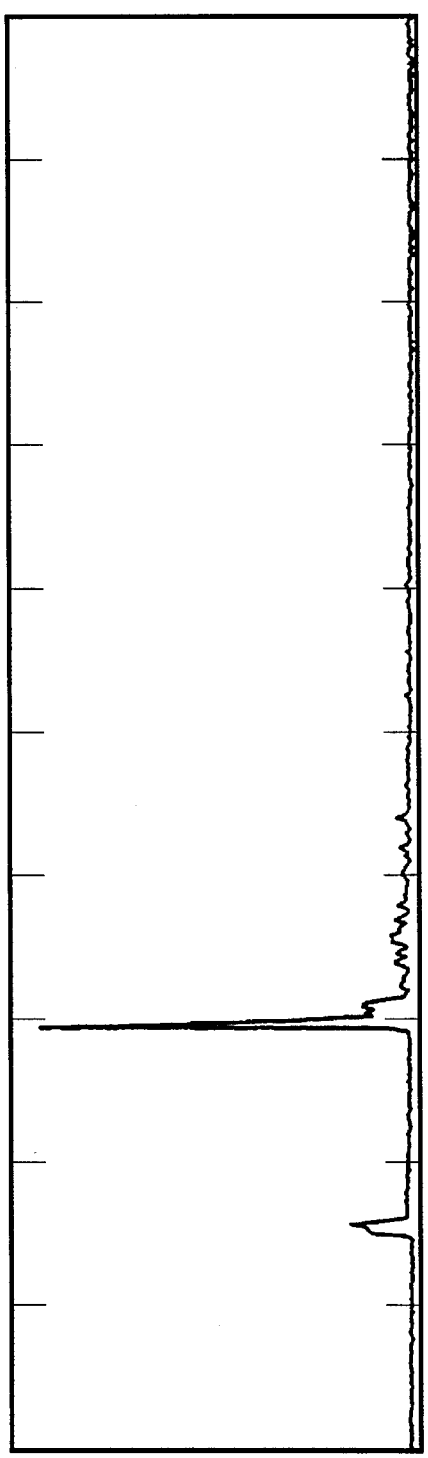
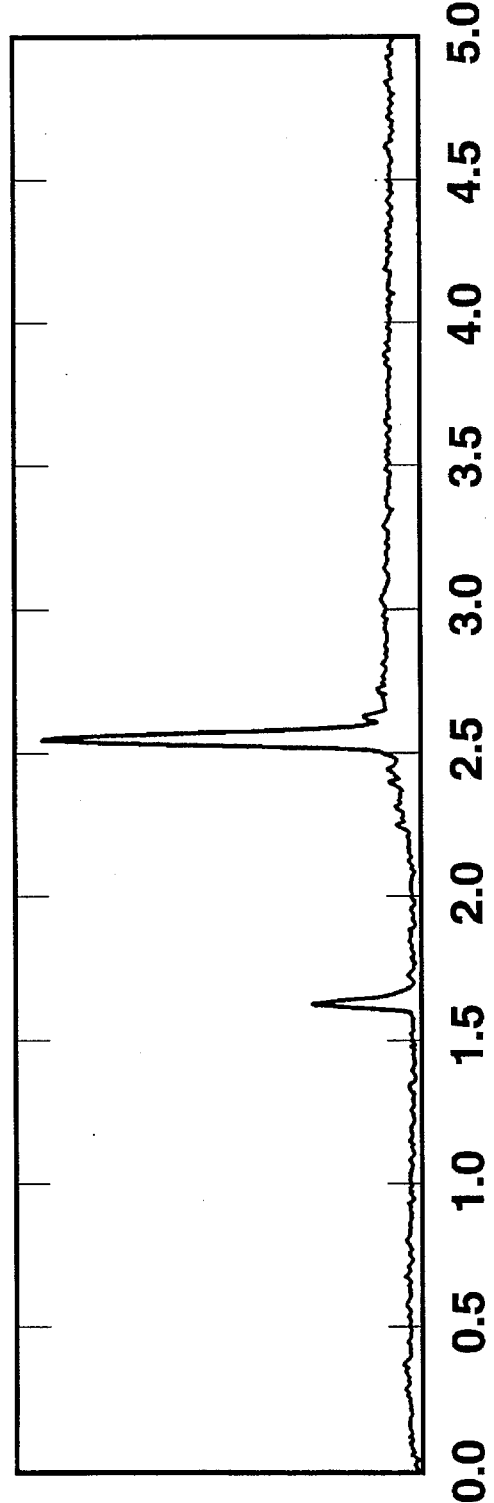
FIG. 2A
FIG. 2B

ELECTROKINETIC PACKING OF CAPILLARY COLUMNS

BACKGROUND OF THE INVENTION

As the miniaturization of analytical instruments continuously proceeds [M. V. Novotny and D. Ishii, Eds., "Microcolumn Separations", Elsevier, Amsterdam, 1985; R. P. W. Scott, Ed., "Small-Bore Liquid Chromatography Columns: Their Properties and Uses", John Wiley & Sons, New York, Chem. Anal., 72, 1984; and Y. Hirata, *J. Microcol. Sep.*, 2 (1990) 214], the packed capillary, also known as microbore, columns with an internal diameter (I.D.) of from 10 to 1000 µm are used increasingly in microseparation techniques, such as microcolumn high performance liquid chromatography (micro-HPLC), supercritical fluid chromatography (SFC) [K. M. Payne, I. L. Davies, K. D. Bartle, K. E. Markides and M. L. Lee, *J. Chromatogr.*, 477 (1989) 161], gas chromatography (GC) [F. J. Yang, *HRC & CC*, 6 (1983) 348], electrochromatography (EC) [C. Yan, D. Schaufelberger and F. Erni,] and multidimensional chromatography [K. D. Bartle, I. L. Davies, M. W. Raynor, A. A. Clifford and J. P. Kithinji, *J. Microcol. Sep.*, 1 (1989) 63]. The increasing demands of packed capillary columns justify the need for searching for more efficient and more economical column-packing technology. Although many efforts have been made in this direction, the slurry packing technique [R. P. W. Scott, Ed., "Small-Bore Liquid Chromatography Columns: Their Properties and Uses", John Wiley & Sons, New York, Chem. Anal., Vol. 72, 1984; and Y. Hirata, *J. Microcol. Sep.*, 2 (1990) 214], so far, has been employed almost exclusively for packing capillary columns. A few reports on a dry packing method [G. Crescentini, F. Bruner, F. Mangani and G. Yafeng, *Anal. Chem.*, 60, (1988) 1659; and J. H. Knox and I. H. Grant, *Chromatographia*, 32 (1991) 317] have also been made.

In the slurry packing method, a suspension of packing material stored in a reservoir is pushed into a column under high pressure (generally from about 200 to 500 atm.). This method is useful for packing capillary columns with fairly good efficiency. However, the involved technique has a number of shortcomings and limitations. One particular disadvantage is that slurry packing is limited to packing particles having a size larger than one micron. Packing of a capillary column with particles of a smaller particle size is important for further improvement in the efficiency of microseparation techniques, especially in electrochromatography. It has been predicted theoretically, and proved experimentally, that the electroosmotic flow is essentially unaffected by a particle size down to at least 1.5 µm. As the particle size is reduced below 1 µm, the plate heights are dominated mainly by the B-term (axial diffusion) in the van Deemter equation.

$$H = A + \frac{B}{U} + Cu \quad (1)$$

Based on the preceding, an efficiency of a million theoretical plates in a time of less than 30 minutes could be achievable in electrochromatography.

However, to pack such a column efficiently with fine particles is a real challenge since, conventionally with slurry packing, extremely high pressure is required. Especially when wide diameter capillaries with a thin wall are being packed, application of such high pressure could be dangerous. Therefore, alternative ways must be found to pack micron and submicron particles in order to improve further the performance of EC in particular, and microseparation in general. In addition, the slurry packing of capillary columns is rather tedious and time consuming because each capillary must be packed individually. Furthermore, the particles (having any particular size distribution) are pushed into a column in a non-selective manner so that the homogeneity of a column packed by the slurry method is rather low.

Electrokinetic separation is known and has developed rapidly since 1981 [Y. Lee, "Capillary Electrophoreses: Principles, practice and applications", Elsevier, Amsterdam, J Chromatogr. Library, Vol. 52, 1992; J. Vindevogel and P. Sandra, "Introduction to Micellar Electrokinetic Chromatography", Hüthig Heidelberg, 1992; J. W. Jorgenson, K. D. Lukacs, *Anal Chem.*, 53 (1981) 1298]. In addition to separation and analysis of compounds, capillary zone electrophoresis (CZE) has been used for characterization and separation of particulate materials, such as submicron polystyrene spheres [B. B. van Orman, G. L. Mcintyre, *Am. Lab.*, Nov., Vol. 66, 1990] and viral particles [S. Hjerén, K. Elenbring, F. Kilar, J. L. Liao, A. J. C. Chen; C. J. Siebert and M. D. Zhu, *J. Chromatogr.*, 403 (1987) 47], as well as colloidal silica sols with diameters in the range of from 5 to 500 nm [R. M. McCormick, *J. Liquid Chromatogr.*, 14 (1991) 939].

During the past three decades, silica-based material has been the dominating stationary phase for high performance liquid chromatography (HPLC). However, it has a serious disadvantage when an alkaline condition is presented because of its limited pH stability above pH 8. What makes things worse is that when positively charged species, e.g., organic bases or certain proteins, are dealt with under the limited alkaline conditions, the interaction of solutes with a negatively charged silica surface (pH >2) causes severe tailing. The effect of the restricted pH stability of a silica matrix is even more pronounced in electrochromatography where a higher pH value usually is desirable for higher mobile phase velocity, which depends on the surface charge of the stationary phase particles.

An aluminum oxide matrix provides an alternative to silica due to its inherent higher pH stability, generally within a pH range of from 2 to 13 [J. J. Pesek, J. E. Sandoval and M. Su, *J. Chromatogr.*, 630 (1993) 95; K. Cabrera, D. Lubda and G. Jung, *Kontakte* (Darmstadt), 1 (1992) 32]. Depending on the pH value of the mobile phase, the chromatographic properties can be changed due to the amphoteric character of aluminum oxide [K. Cabrera, D. Lubda and G. Jung, *Kontakte* (Darmstadt), 1 (1992) 32]. Particularly in electrochromatography, a column packed with an aluminum oxide-based stationary phase is useful as a multi-purpose column since the sign of the surface charge on the particles, and consequently the direction of electroosmotic flow (EOF) can be altered by varying the pH value of the mobile phase.

SUMMARY OF THE INVENTION

The previously mentioned problems are overcome by using the electrokinetic packing method in accord with which (a) there is no high back pressure as is generated in slurry packing because particles under a strong electric field are moved by electroosmotic flow in the column and move with their own electrophoretic mobility, if charged; (b) several capillaries can be packed simultaneously and, consequently, the electrokinetic packing method is more efficient and economical; and (c) to some extent, the electrokinetically packed column is more homogeneous (in cross section) because the particles move into the column according to their charge-to-size ratio, thus forming a packing which is novel in particle orientation.

The present invention relates to electrokinetic packing of capillary columns, and provides a novel column packing technology. Capillary columns, such as those of fused silica, and having an internal diameter of from less than 10 microns to about 500 microns or more are packed with, e.g., 3 μm aluminum oxide-based $C_{18}$ reversed phase suspended in a mobile phase composed of methanol and 2 mM $NaH_2PO_4$ buffer by applying high electric voltage.

There are a number of distinct aspects to this invention:

a) particles of packing arranged in a capillary column are substantially homogeneous in cross section with regard to their charge-to-size ratio; this is particularly advantageous for chromatography, as it provides for higher efficiency and better resolution;

b) Electrokinetic packing permits packing capillaries with particles having smaller diameters;

c) apparatus has been especially designed to facilitate electrokinetic packing of capillary columns; and d) use of electricity to pack microbore capillary columns.

BRIEF DESCRIPTION OF THE DRAWINGS

FIG. 2. Electrochromatogram for 3 μm Octadecyl Alumina (Spherisorb™ $A_3$ PC18) particles with a 60 cm×75 μm capillary (detection window at center). FIG. 2a Mobile phase: 80:20 (v/v) $CH_3CN$—2 mM $NaH_2PO_4$ (pH=4.5), Applied voltage 40 kV (1.0 μA), Injection 10 kV/3 sec. FIG. 2b 2 mM $NaH_2PO_4$ buffer, Applied voltage 30 kV (4.6 μA), Injection 5 kV/5 sec.

DETAILED DESCRIPTION OF THE INVENTION

Figure 1:
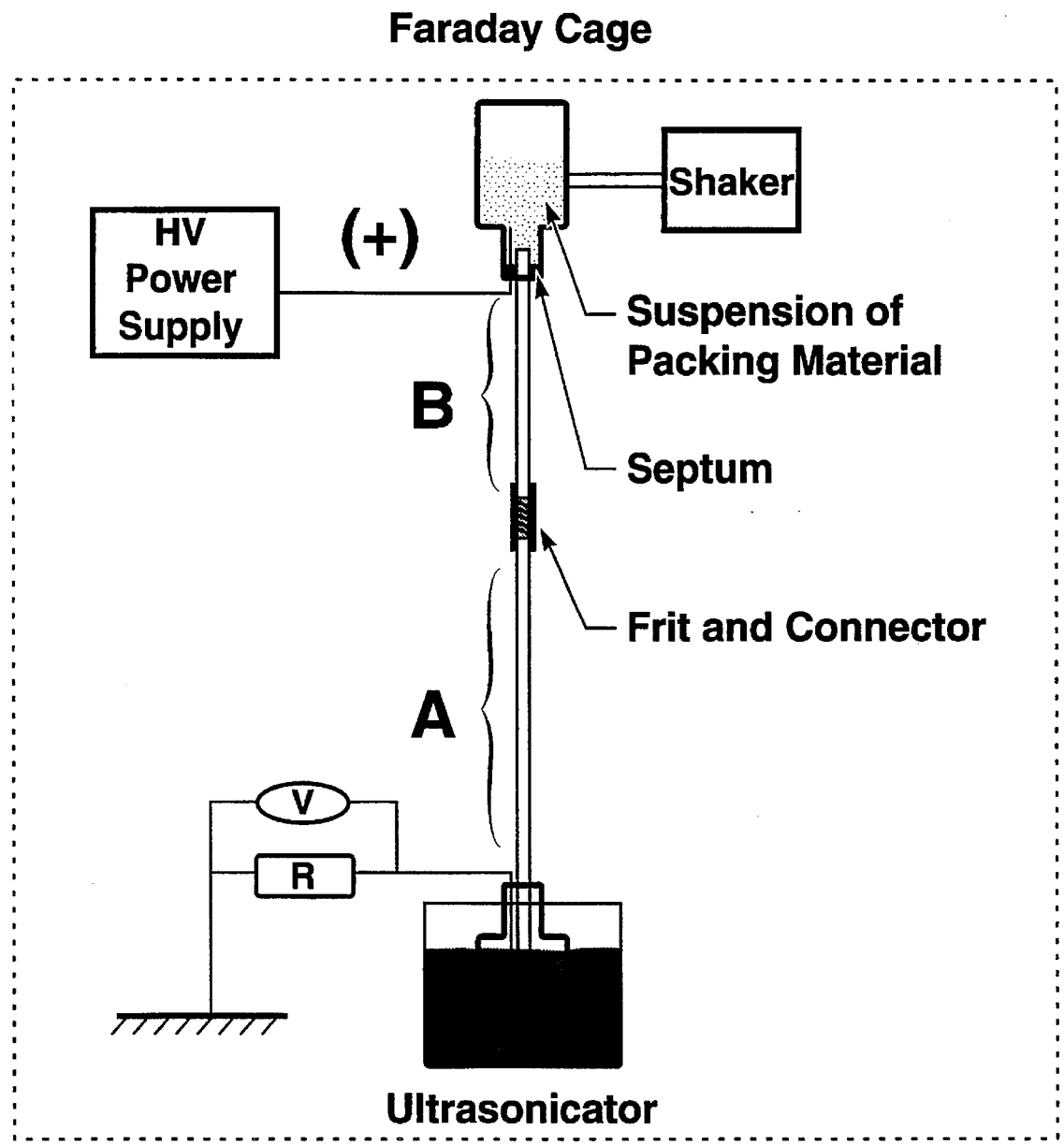
FIG. 1. A schematic diagram of apparatus for electrokinetic packing of capillary columns.

Particles in a capillary filled with a particular mobile phase move, if charged, with their own electrophoretic mobility and are also moved by electroosmotic flow (EOF) through the column. The migration velocity $V_{ep}$ of a charge-carrying particle is dependent on electric field strength E and electrophoretic mobility $\mu_{ep}$ which, in turn, is a complex function of the particle radius r, surface charge density q, medium viscosity η, and the thickness k and polarizability of the electric double layer. For the purpose of the present invention, it may be sufficient to use the simplest description for a rigid spherical particle when the double layer is both thin and unpolarized [J. Vindevogel and P. Sandra, "Introduction to Micellar Electrokinetic Chromatography", Hüthig Heidelberg, 1992]:

$$V_{ep} = \mu_{ep} E = \frac{q}{6\pi r \eta} E \qquad (2)$$

If the ζ (zeta) potential and permitivity ε of the medium are used, $$\mu_{ep} = \frac{\epsilon \zeta}{4\pi \eta} = \frac{2\epsilon_0 \epsilon_f \zeta}{3\eta} \qquad (3)$$

wherein $\epsilon_o$ and $\epsilon_f$ are the permitivity of vacuum ($8.85 \times 10^{-12}$ $C^2/N \cdot m^2$) and dielectric constant.

The electrophoretic mobility of nonuniformly charged particles with a polarized double layer can be reduced due to a significant rate of transport of counterions within the double layer, resulting in a reduced gradient of electrical potential along the particle's surface and a countergradient of electrolyte concentration [Y. E. Solomentsev, Y. Pawar and J. L. Anderson, *J. Colloid Interface Sci.*, 158 (1993) 1]. In fact, the direction of the electrophoretic migration can even be reversed by the polarization effect, a phenomenon called "diffusiophoresis" [T. G. M. van de Ven, P. Warszynski and S. S. Dukhin, *J. Colloid Interface Sci.*, 157 (1993) 328].

In addition, an electrically charged spherical particle moving in the vicinity of a wall or other particles is subject to a repulsive "electrokinetic lift force" [T. G. M. van de Yen, P. Warszynski and S. S. Dukhin, *J. Colloid Interface Sci.*, 157 (1993) 328] caused by the breaking of the axial symmetry of the hydrodynamic and electric fields surrounding the particle. When the ratio of the minimum gap width δ to the particle radius r is very small (δ<r), the electrokinetic lift force is given by $$F = 0.38\pi\epsilon^3 \left( \frac{v\zeta}{K} \right)^2 \frac{I}{\delta^3} \qquad (4)$$

wherein v is the velocity of the particle and K is the specific conductivity of the medium. It is clear that this force increases rapidly with the decrease of the gap width, which is unfavorable to electrokinetic packing.

The electrical double layer formed at the interface between a charged surface and an electrolyte induces electroosmotic flow, the direction of which is determined by the charge of the excess ions in the solution. The linear velocity of EOF is given by $$v_{eo} = \mu_{eo} E = \frac{\epsilon_0 \epsilon_f \zeta}{\eta} E \qquad (5)$$

If the sign of the charges on the particles in the capillary is the same as that on the surface of the internal wall of the capillary, the direction of the particle movement is against the direction of the EOF, and vice versa. In the case of a fused silica capillary, the acidic silanol groups on the surface lose protons (above pH 2), thus causing a positive charge excess in the solution and, therefore, inducing EOF to the cathode. Under the experimental conditions, the surface of the aluminum oxide-based $C_{18}$ reversed phase (pK 6.5 according to the manufacturer) is positively charged. Therefore, the particles move in the same direction with EOF, i.e., to the cathode. The local EOF (to the anode) caused by the packed part of $Al_2O_3$—$C_{18}$ particles is against the bulk EOF in the column and also against the electrophoretic migration of the particles.

Although repeated references are made to alumina-based $C_{18}$ reversed phase packing particles, such is merely illustrative. Any suitable capillary packing material is optionally employed. The most common such materials are either alumina-based, silica-based or polystyrene-based normal or reversed phase packing material. The packing material particles are preferably positively charged, but are optionally either uncharged or negatively charged. Reference to carbon loading refers to ligands bound to particle surfaces The designation "$C_{18}$" refers to a hydrocarbon ligand having an 18 carbon chain.

As capillary packing is involved, particles of the packing material must have small enough diameters to serve their intended purpose. Although the subject electrokinetic process is applicable to packing particles having a large range of sizes, it is particularly advantageous for particles of sizes smaller than those normally suitable for other packing methods. The electrokinetic packing method is particularly suitable for packing particles having diameters of less than 10 microns, particularly for such particles having diameters of less than 5 microns, and even more particularly for particles having diameters of at most three microns or even those having diameters of at most 1 micron.

The capillary columns that are readily packed by the electrokinetic method are virtually unlimited in internal diameter; virtually any capillary column can be packed with this method, which is particularly advantageous for capillary columns having internal diameters of from less than 10 microns to more than 500 microns.

EXAMPLES

Materials

Fused silica capillaries with 50 μm I.D. (365 μm O.D.), 75 μm I.D. (365 μm O.D.) and 320 μm I.D. (450 μm O.D.), respectively, were obtained from Polymicro Technologies (Phoenix, Ariz., USA).

Aluminum oxide-based $C_{18}$ reversed phase, Spherisorb™ A3 PC18, (stable at pH 13) with 3 μm diameter and 7% carbon loading was obtained from Phase Separations (Norwalk, Conn., USA). The stationary phase (packing) material had a pK value of 6.5 according to the manufacturer. Teflon tubing for column connections (250 μm I.D.) was obtained from LC Packings (Baarsjesweg 154, 1057 HM, Amsterdam, The Netherlands).

Solvents and solutes of the test mixture, consisting of thiourea, benzyl alcohol and benzaldehyde, were purchased from Merck (D-6100, Darmstadt, Germany).

Terbinafine hydrochloride (drug substance of Lamisil®) and three of its degradation products, 1=(E)-6,6-dimethyl-hept-2-en, 4-in-al, 2=N-methyl-1-naphthalenethanamine, 3=(Z)-N-(6,6-dimethyl- 2-heptan-4-ynyl)-N-methyl-1-napthalenemethanamine, were obtained from Sandoz Pharma. Ltd., Analytical R&D. The mobile phase was prepared by mixing 4 mM sodium tetraborate (pH=9.1) or 2 mM sodium dihydrogen phosphate (pH=4.5) with acetonitrile or methanol, followed by filtration through a nylon 66 membrane (0.22 μm pore size) and by degassing (ultrasonic bath and helium).

The degassing is effected, e.g., merely by bubbling helium through the solution. The ultrasonic bath can be any such bath; it is used merely as an aid, and its details are not critical.

FIG. 1 is a schematic representation of apparatus suitable for the electrokinetic packing of capillary columns. The apparatus is employed to test electrokinetically packed columns for the Separation of a test mixture and pharmaceutical compounds. The mobile phase used for the separation was 4 mM sodium tetraborate (pH=9.1) mixed with acetonitrile or methanol ranging from 0 to 80% (v/v). For column packing, only 2 mM sodium dihydrogen phosphate (pH=4.5) buffer and acetonitrile or methanol were used. The apparatus and procedures for separation were also used for the study of the electrokinetic migration behavior of the stationary material by injecting a narrow zone of a suspension of Spherisorb™ A3 PC18 into the capillary. Detection was carried out at 220 nm via turbidity (particles) and UV absorption (Thiourea).

Procedure

Capillary columns with, respectively, 50, 75 and 320 μm I.D. were packed electrokinetically. The packing of one capillary column was carried out as follows:

(1) A piece of capillary (40 cm×75 μm I.D., capillary A) was cut and a porous outlet-frit was sintered [J. H. Knox and I. H. Grant, *Chromatographia*, 32 (1991) 317] by gentle heating of about 0.5 mm of the end filled with a paste of 4 μm spherical silica gel wetted with a dilute sodium silicate solution. The gentle heating is merely that adequate to eliminate liquid and to fuse frit particles, leaving a filter sufficient to retain packing particles while permitting liquid to pass through.

(2) The end-frit of capillary A was connected to another piece of capillary (20 cm×75 μm I.D., capillary B) by a teflon connector [C. Yan, D. Schaufelberger and F. Erni].

(3) A suspension was prepared by weighing out 300 mg of Spherisorb™ A3 PC18 in a vial, to which about 5 ml of methanol containing 3% (v/v) 2 mM $NaH_2PO_4$ (pH=4.5) was added. The vial, closed with a cap and a septum, was put in an ultrasonic bath for about 10 minutes to suspend packing particles in methanol and then mounted upside-down in the packing apparatus as the anode vial, as in FIG. 1. The ultrasonic bath is any ultrasonic bath; its sole purpose is to suspend the packing particles in solvent. Further details of the ultrasonic bath are not critical.

(4) A cathode vial filled with pure 2 mM $NaH_2PO_4$ buffer is placed in an ultrasonic bath. Details of the ultrasonic bath are not in any critical; this bath is employed solely to assist in vibrating the capillary tube to avoid clogging. (When particles of the packing material are negatively charged, e.g. silica particles, the anode and cathode vials are reversed).

(5) The connected capillaries were rinsed, respectively, with 2 mM $NaH_2PO_4$ buffer and acetonitrile by using a syringe, then mounted in the equipment (FIG. 1).

(6) The voltage was gradually increased from 2 kV to 30 kV in 5 minutes, and then kept constant. The HV (high electric voltage) power supply shown in FIG. 1 must be adequate to generate the specified voltage in the noted time. Further details of the power supply are not critical.

(7) The ultrasonic bath and shaker were switched on and continued until capillary B was visibly packed (about 10 minutes). The shaker for the vial containing the packing suspension is, optionally, any shaker capable of maintaining packing particles in suspension.

(8) The electric power, ultrasonic bath and shaker were switched off and the column was removed from the equipment.

(9) An inlet-frit was sintered in the same manner as described for the outlet-frit.

(10) The packed capillary column was visually inspected by placing it on a glass surface between a light source and a magnifier.

This procedure was also used for packing three capillary columns simultaneously.

Results

FIG. 2 illustrates electropherograms for the 3 µm particles using pure 2 mM $NaH_2PO_4$ buffer and thiourea as EOF marker. The movement of the positively charged particles is obviously retarded due to adsorptive and electrostatic interactions between the particles and the internal surface of the capillary wall. The first peak is that for thiourea; the second, packing material.

Figure 3:
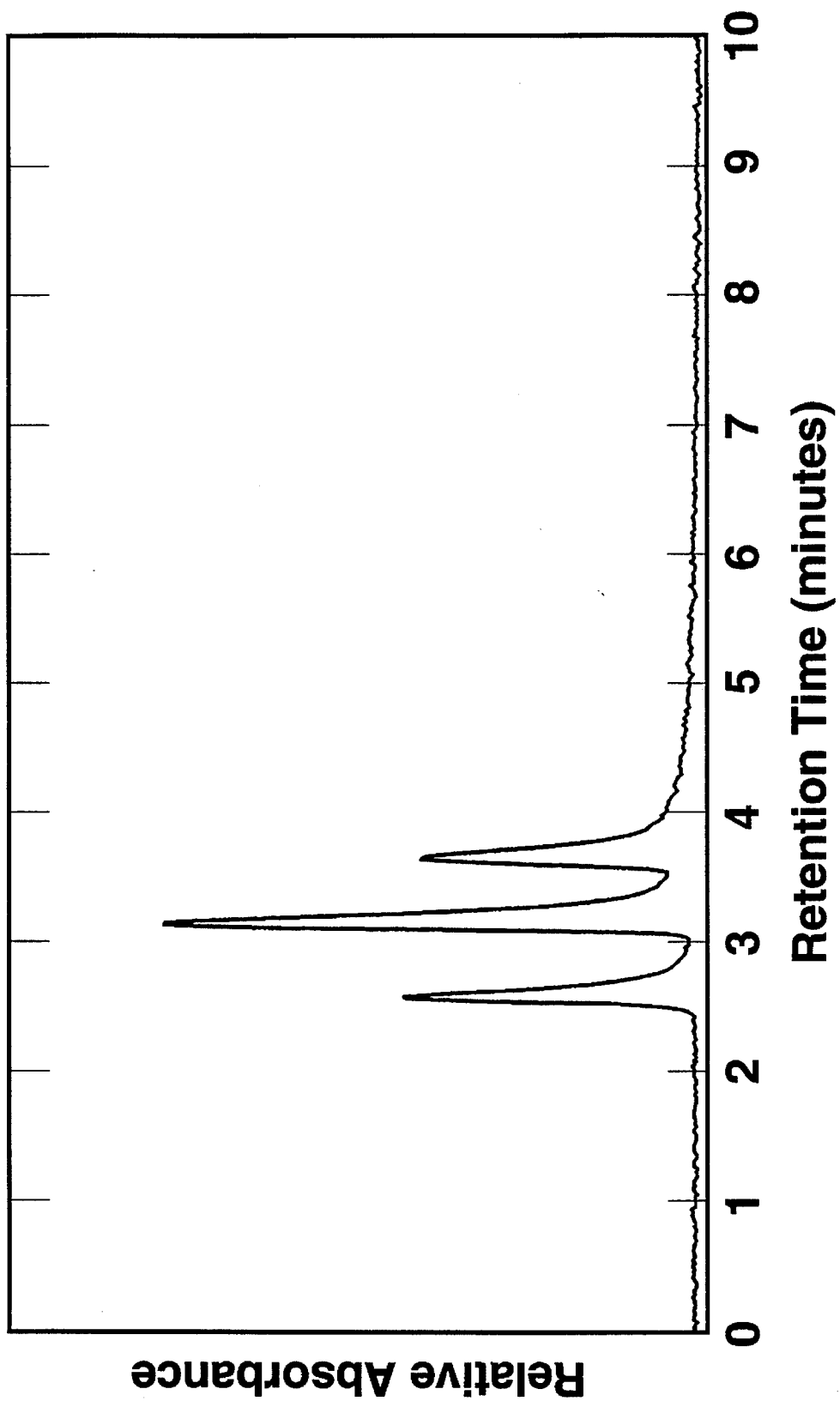
FIG. 3. Electrochromatographic Separation of test mixture on a 25 cm×50 μm I.D. column packed electrokinetically with 3 μm Octadecyl Alumina. Mobile phase: 40:60 (v/v) $CH_3CN$—4 mM sodium tetraborate (pH=9.1). Applied voltage 20 kV (2.15 μA), Injection 5 kV/5 sec. Solutes in the order of elution: (1) thiourea, (2) benzylalcohol, (3) benzaldehyde.

The electrokinetically packed columns were tested for separation of a test mixture consisting of thiourea, benzylalcohol and benzaldehyde, as well as for pharmaceutical compounds (Lamisil®) using electrochromatography. FIG. 3 is an electrochromatogram obtained on a 50 µm I.D. column (15 cm packed)/25 cm to detector) using a mobile phase of 40% (v/v) $CH_3CN$ in 4 mM $Na_2B_4O_7$ buffer (pH=9.1). Note that the surface charge of the stationary phase is reversed (from positive to negative) and the EOF in electrochromatography goes to the cathode. The reduced plate heights are 14, 16 and 14 for thiourea, benzylalcohol and benzaldehyde, respectively.

Figure 4:
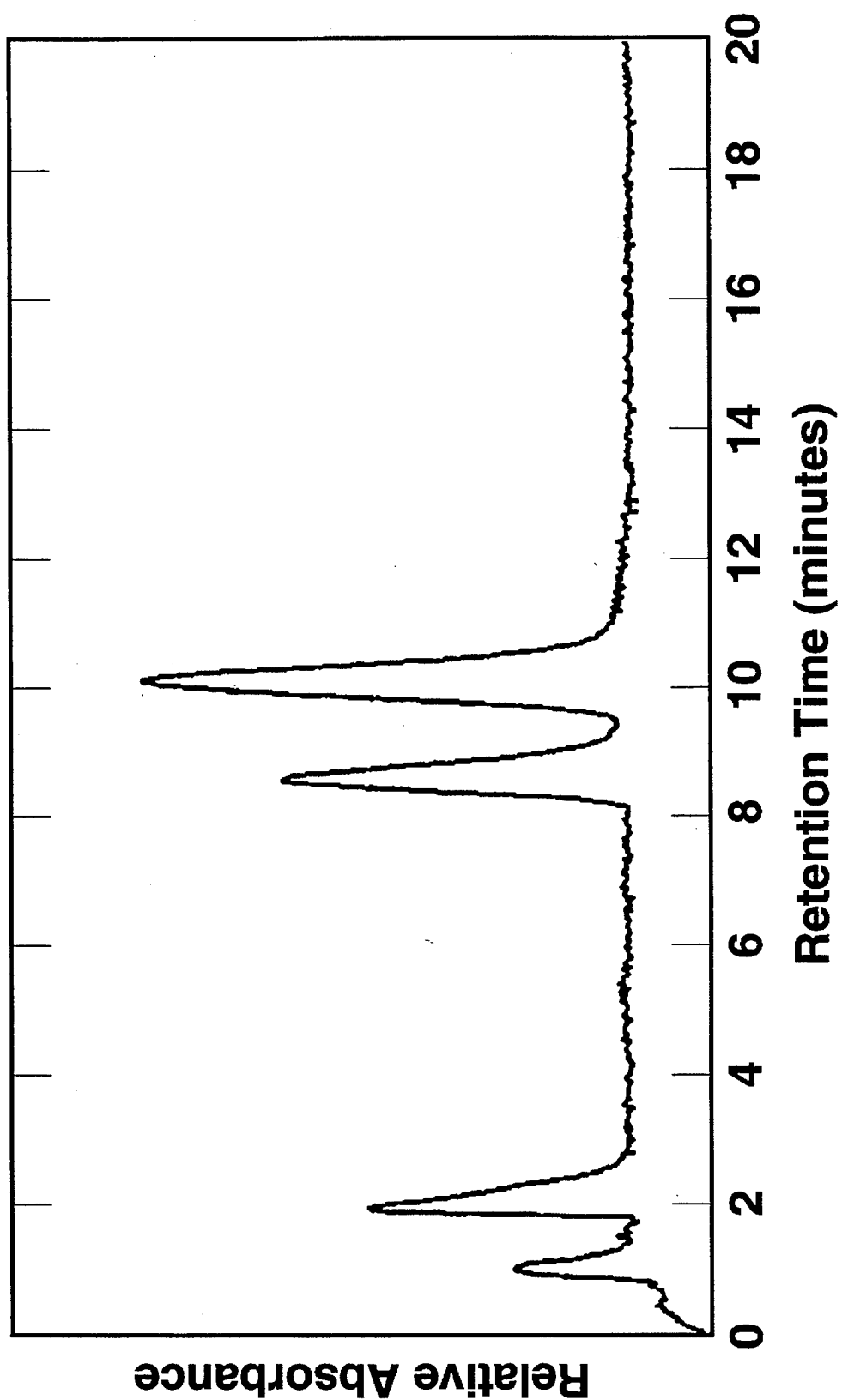
FIG. 4. Electrochromatographic Separation of terbinafine and three of its potential degradation products. The same column as in FIG. 2a. Mobile phase: 50:47:3 (v/v/v) CHaCN—4 mM sodium tetraborate-tetrahydrofuran, pH value adjusted to 12 by 1N NaOH. Applied voltage 30 kV (9.0 μA), Injection 5 kV/5 sec. Solutes in the order of elution: (1) 1, (2) 2, (3) 3, (4) Terbinafine (see page 11).

The usefulness of electrokinetic packed capillary columns is further illustrated by the separation of compounds of pharmaceutical interest. FIG. 4 shows the chromatograms from the separation of the new antifungal compound terbinafine, from three of its potential degradation products. Electrochromatography was carried out by applying a voltage of 22 kV with a mobile phase of $CH_3CN$ with 4 mM $Na_2B_4O_7$ buffer plus tetrahydrofuran (50/47/3, v/v/v). The pH value was adjusted from 9.1 to 12 with 1N NaOH in order to reduce possible solute-wall interaction. With the aluminum oxide-based packings the stationary phase can tolerate high alkaline environment. This is a favorable condition for particular separations.

In another test using micron-HPLC with an electrokinetically packed column (10 cm/17 cm×75 µm I.D.) and with a mobile phase of 20% $CH_3CN$ in 2 mM $NaH_2PO_4$ buffer (pH=4.5), better efficiency was achieved. The reduced plate heights obtained in a particular separation are 3.5, 3.7 and 5.4 for thiourea, benzylalcohol and benzaldehyde, respectively. Since the internal surface of the capillary is different from the surface of the packing particles, the profile of electroosmotic flow in the column may not be plug-like, which might account for the relatively low efficiency of the column in electrochromatography. Other factors such as quality of frits and column connections may also contribute to peak broadening.

Electrokinetic packing of capillary columns may have a positive impact on electrochromatography, a promising technique that could unify the excellent efficiency of CZE and good selectivity of micro-HPLC [C. Yan, D. Schaufelberger and F. Erni,; and J. H. Knox and I. H. Grant, *Chromatographia*, 32 (1991) 317]. However, as Vindevogel and Sandra, supra, pointed out that further reduction of the internal diameter makes packing much more difficult, a gain in popularity of electrochromatography with packed columns has to be expected if a technological breakthrough permits the fabrication and utilization of packed columns for CZE to be more easily accomplished.

With the electrokinetic packing method, it may be possible to perform electrochromatography as in CZE with dynamic coating. Stated another way, electrochromatography may proceed after the stationary phase is packed without drying the column. This would significantly reduce the column cost as well as the tediousness of conventional slurry packing.

It should be noted that this new column packing method can be used only for packing capillary columns made of non-conductive or semi-conductive materials. To take advantage of electrokinetic packing, either the internal surface of the capillary or the surface of the packing material has to be charged.

Under high electric voltage, plural capillary columns can be packed simultaneously using electroosmotic flow (EOF) induced by an electric double layer on the capillary wall and the electrophoretic mobility of an aluminum oxide-based reversed phase. The electrokinetically packed capillary columns are useful for separation and analysis of test mixtures and of pharmaceutical compounds in both, electrochromatography and micro-HPLC.

In general, any neutral (uncharged), positively-charged or negatively-charged particles can be packed into fused silica capillaries using the electrokinetic method. Columns can be partially packed.

With this new packing method, micron or even submicron particles may be packed in capillary columns. This will further improve the column efficiency currently achievable in micro-HPLC and electrochromatography.

The invention and its advantages will be readily understood from the foregoing description. Various changes may be made in the compositions, the packed columns, the apparatus and the methods without departing from the spirit and/or scope of the invention or sacrificing its material advantages, the process, apparatus, compositions and products hereinbefore described being merely illustrative of preferred embodiments of the invention.

What is claimed is:

1. A method of electrokinetic packing of particles in a capillary column having two ends, which comprises embedding one end of the column in a suspension of packing material containing the particles, imposing a sufficient voltage difference over the two column ends to move the packing material into the capillary column, and maintaining the voltage until said capillary column is adequately packed.

2. A method of claim 1 wherein particles in the packing material are no larger than 3 microns in diameter.

3. A method of claim 1 wherein particles in the packing material are no larger than 1 micron in diameter.

4. A method of claim 1 wherein the particles are positively-charged particles.

5. A method of claim 1 wherein the particles are uncharged particles.

6. A method of claim 1 wherein the particles are negatively-charged particles.

7. A method of claim 1 wherein the packing material is moved by electroosmotic flow and particles in the packing material are less than 10 microns in diameter.

8. A method of claim 7 wherein the particles are positively-charged particles.

9. A method of claim 7 wherein the particles are negatively-charged particles.

10. A method of claim 1 wherein the packing material is moved by electrophoretic mobility and particles in the packing material are less than 10 microns in diameter.

11. A method of claim 10 wherein the particles are positively-charged particles.

12. A method of claim 10 wherein the particles are negatively-charged particles.

* * * * *